(12) United States Patent
Jarjour et al.

(10) Patent No.: US 8,839,676 B2
(45) Date of Patent: Sep. 23, 2014

(54) STRUCTURAL ELEMENT FOR AN ORTHOPEDIC DEVICE

(75) Inventors: Wissam Jarjour, Lübben (DE); Olaf Kroll-Orywahl, Göttingen (DE); Matthias Schilling, Weißenborn-Lüderode (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 309 days.

(21) Appl. No.: 13/263,316

(22) PCT Filed: Apr. 20, 2010

(86) PCT No.: PCT/DE2010/000457
§ 371 (c)(1),
(2), (4) Date: Oct. 6, 2011

(87) PCT Pub. No.: WO2010/121603
PCT Pub. Date: Oct. 28, 2010

(65) Prior Publication Data
US 2012/0036939 A1    Feb. 16, 2012

(30) Foreign Application Priority Data

Apr. 22, 2009  (DE) .......................... 10 2009 018 179

(51) Int. Cl.
*G01B 7/16*   (2006.01)
*A61F 5/01*   (2006.01)
*A61F 2/76*   (2006.01)

(52) U.S. Cl.
CPC ................. *A61F 5/01* (2013.01); *A61F 5/0123* (2013.01); *A61F 2002/7635* (2013.01)

USPC ........................................................ 73/774

(58) Field of Classification Search
CPC ..... G01B 7/16; A61B 2562/12; A61C 8/0006; G01D 5/12
USPC .................................... 73/760, 768, 774, 775
See application file for complete search history.

(56) References Cited

U.S. PATENT DOCUMENTS 5,840,047 A    11/1998  Stedham
6,324,432 B1 *  11/2001  Rigaux et al. ................... 607/62
(Continued)

FOREIGN PATENT DOCUMENTS

CN   102036628 A   4/2011
DE    10201134 A1  7/2003
(Continued)

OTHER PUBLICATIONS

Chinese Search Report for Patent Application No. 201080017910.0, mailed May 22, 2013.
PCT International Search Report for International Application No. PCT/DE2010/00457, mailed Aug. 6, 2010.

*Primary Examiner* — Max Noori
(74) *Attorney, Agent, or Firm* — Holland & Hart

(57) ABSTRACT

The invention relates to a structural element for an orthopedic device, comprising at least one sensor (2) disposed in or on the structural element (1) and connected by means of conductors (13) for transferring energy and/or sensor signals, wherein the conductors (13) are integrated in the structural element (1), extend along an end area (A) of the structural element (1), and open into the end area (A), forming contact surfaces (3) there.

21 Claims, 5 Drawing Sheets

(56) References Cited

U.S. PATENT DOCUMENTS

| | | |
|---|---|---|
| 7,552,644 B2 * | 6/2009 | Haase et al. .................... 73/768 |
| 7,578,799 B2 | 8/2009 | Thorsteinsson et al. |
| 7,878,055 B2 | 2/2011 | Balzano |
| 7,997,007 B2 | 8/2011 | Sanabria-Hernandez |
| 8,122,772 B2 * | 2/2012 | Clausen et al. ................ 73/812 |
| 8,234,929 B2 * | 8/2012 | Clark et al. ..................... 73/776 |
| 2010/0101118 A1 | 4/2010 | Guenther |
| 2010/0262055 A1 * | 10/2010 | Schilling et al. ............... 602/16 |
| 2011/0066255 A1 | 3/2011 | Friesen et al. |

FOREIGN PATENT DOCUMENTS

| | | |
|---|---|---|
| DE | 102004027252 A1 | 12/2005 |
| DE | 102004030570 A1 | 1/2006 |
| DE | 102006029938 A1 | 10/2007 |
| DE | 102007051652 A1 | 8/2008 |
| WO | 2005058211 A2 | 6/2005 |
| WO | 2007107150 A1 | 9/2007 |

* cited by examiner

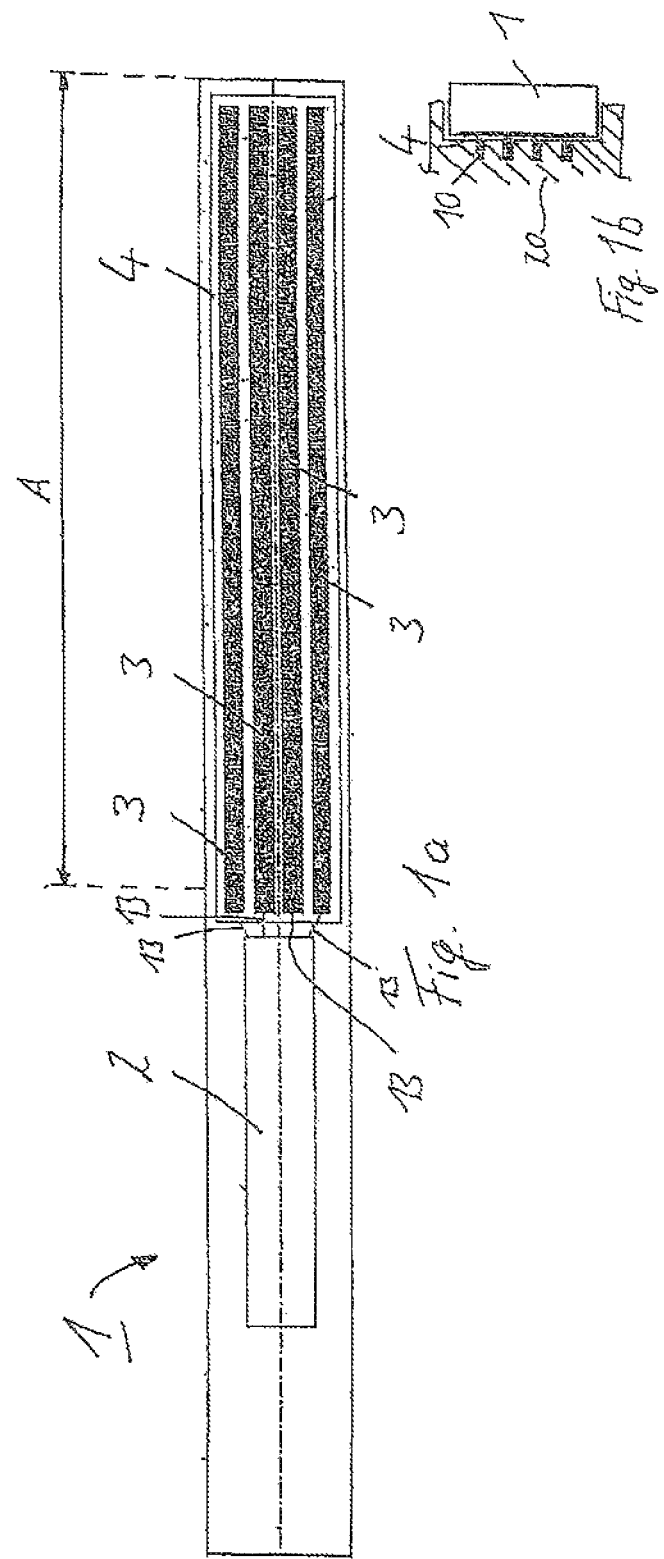

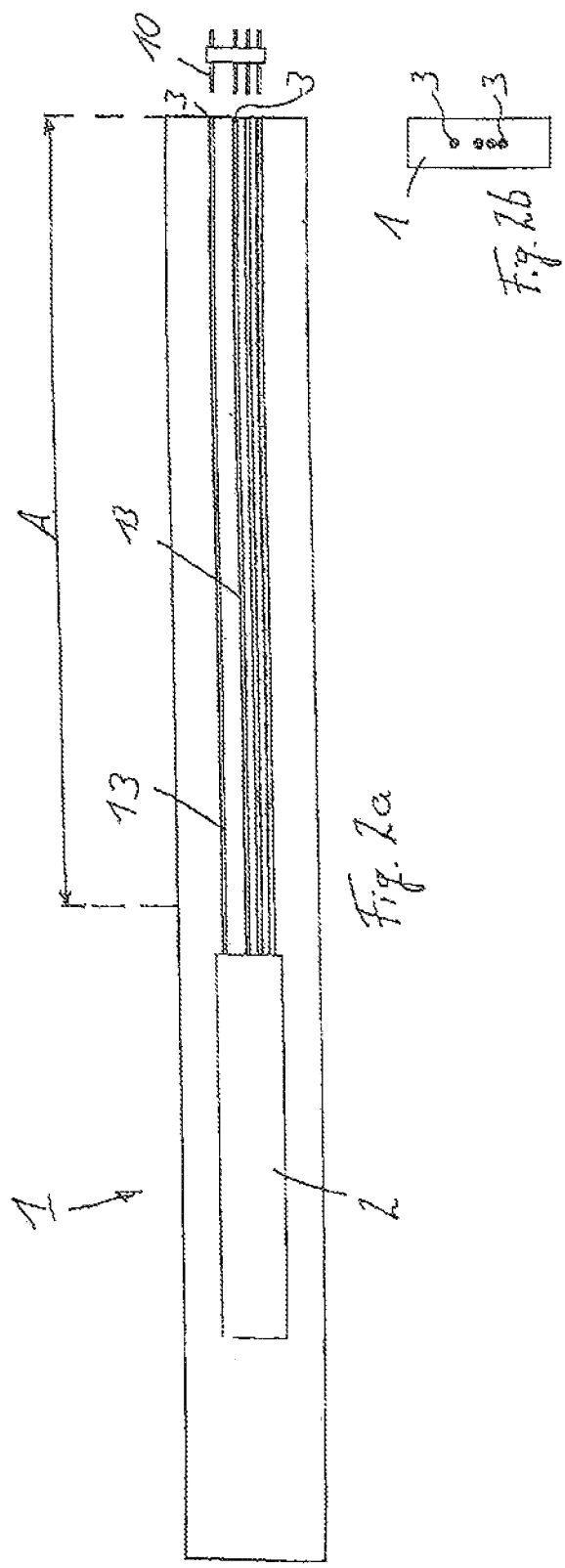

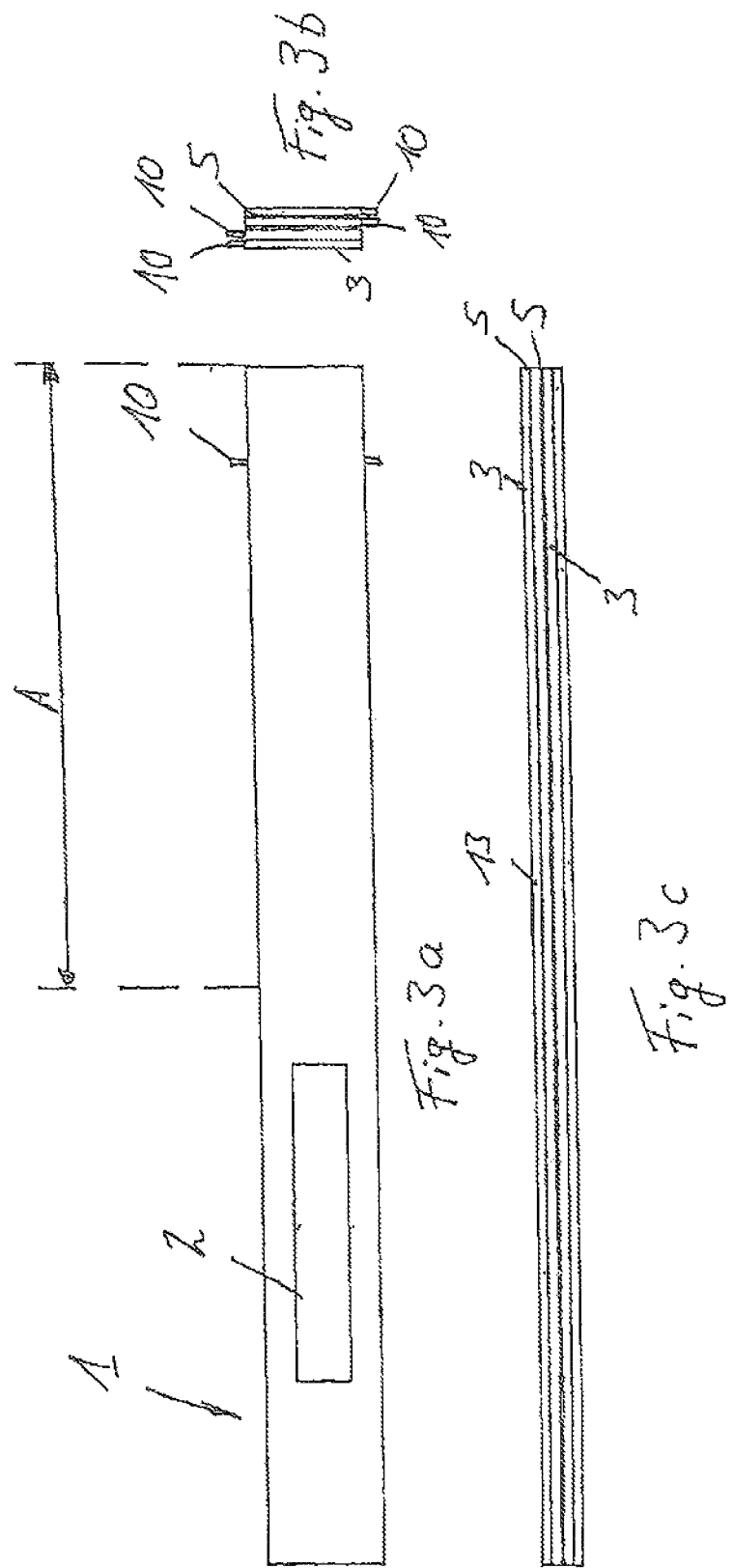

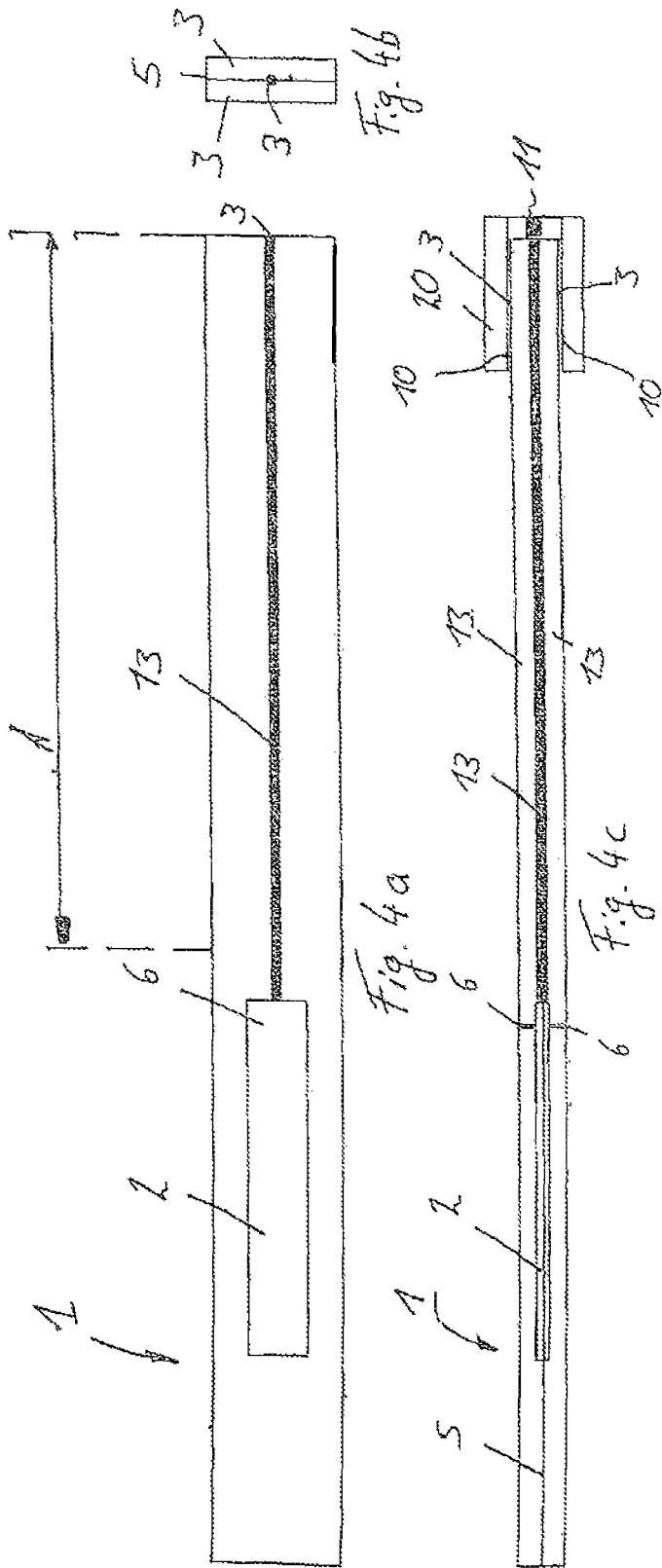

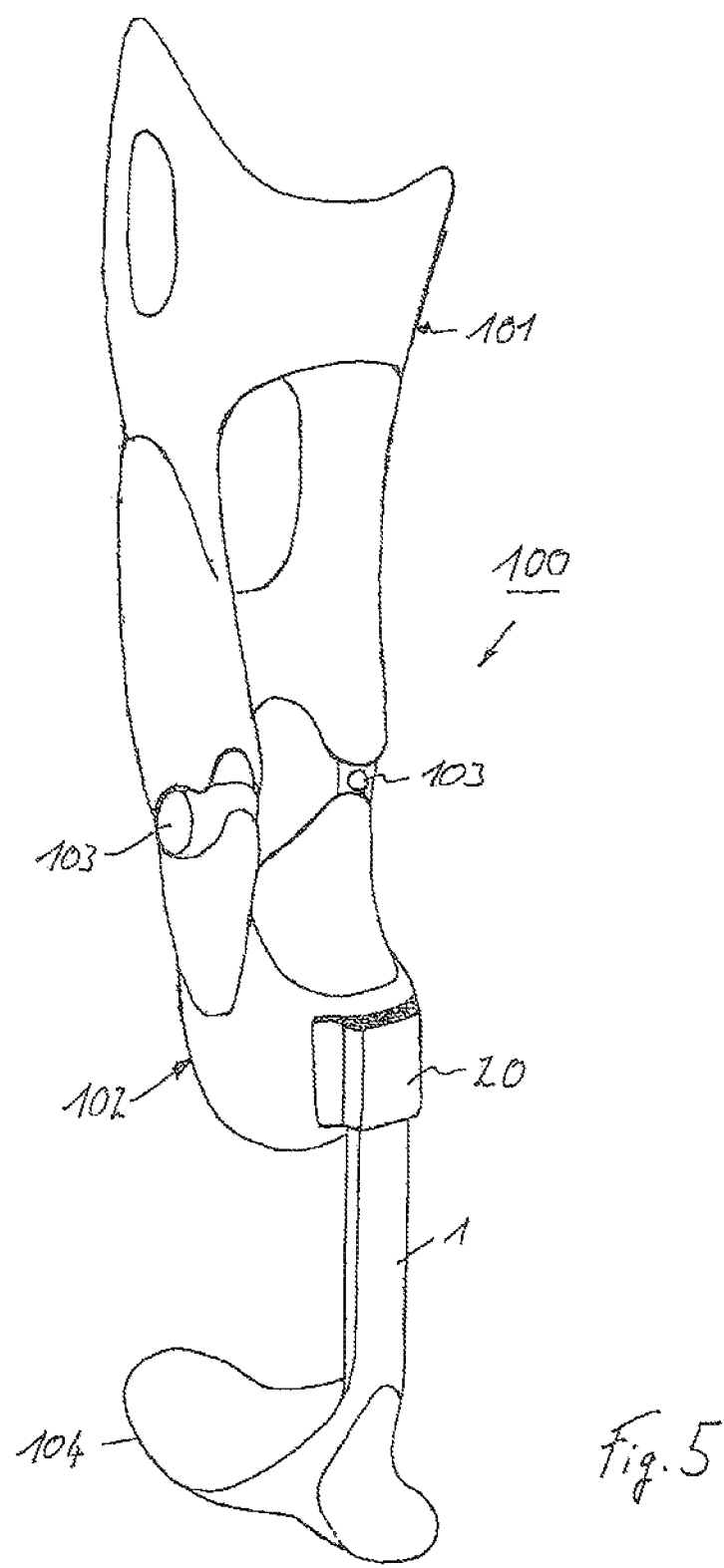

STRUCTURAL ELEMENT FOR AN ORTHOPEDIC DEVICE

The invention relates to a structural element for an orthopedic device, more particularly for an orthosis or a prosthesis, having at least one sensor integrated into the structural element, which sensor is connected to conductors for transmitting energy and/or sensor signals, and an orthopedic device with such a structural element.

Orthopedic devices occasionally require a plurality of components to be interconnected. A distal component can be interconnected with a proximal component in a resilient fashion, for example a knee part and a foot part of a knee-ankle-foot orthosis.

In the context of an ankle foot orthosis, DE 10 2004 027 252 A1 discloses the use of a beam spring made of a fiber-reinforced composite material. Attachment devices for fixing the spring to the foot and to the lower leg are arranged on the arced beam spring.

Attaching a foot part of a knee-ankle-foot orthosis to a lower leg has been disclosed in WO 2005/058211 A2. The lower-leg part is in this case formed from two metal struts that are kept apart from one another. A swivel pin, by means of which a foot part is connected to the struts such that it can swivel, is arranged at the distal end of every metal strut.

US 2008/0039756 A1 describes a knee-ankle-foot orthosis in which the lower-leg part is formed by a rigid frame, on which a foot part for supporting a foot is arranged via a foot joint. The foot part can be moved via an actuator.

In addition to an application in a knee-ankle-foot orthosis, the structural elements can also be used in prostheses for the lower or upper extremities and for orthoses in the torso region or on the upper extremities.

In order to obtain information relating to the forces occurring in the structural element or being transmitted by the structural element, there is the option of arranging a sensor on or in the structural element, which sensor outputs the sensor data to a receiver. In addition to wireless transmission, provision is usually made for conductors for transmitting energy and/or sensor signals to be physically connected to the sensor, and for these conductors needing to be routed out of the structural element. Plug-in contacts are generally arranged at the end of these conductors in order to be able to read out the sensor data after the structural element was installed.

An object of the present invention is to provide a structural element with a modifiable length, which can be used on or in corresponding receptacle devices of orthopedic components, wherein the length of the structural element can be matched to the individual conditions of the user of the orthopedic device.

According to the invention, this object is achieved by a structural element having the features of the main claim. Advantageous embodiments and developments of the invention are listed in the dependent claims. The structural element according to the invention for an orthopedic device, more particularly for an orthosis or a prosthesis, which structural element has at least one e.g. integrated sensor arranged in or on the structural element, which sensor is connected to conductors for transmitting energy and/or sensor signals, provides for the conductors to be integrated into the structural element and extend along at least one end region of the structural element. The conductors open out into the end region and form contact surfaces there, via which the sensor signal can be tapped or energy can be supplied or dissipated. Since the contact surfaces extend along the outer region over a certain longitudinal extent, or since they are formed in the end region, there can be a simple length modification in the region of the contact surfaces by simply removing the excessive length of the structural element. In the process, the spatial assignment of the contact surfaces remains unchanged, and so the correspondingly arranged contacts on the components to be arranged on the structural element can remain unchanged.

The structural element is preferably embodied as a spring element, for example as a beam spring, in order to interconnect two components whilst allowing a small resilient displacement with respect to one another.

The sensor is preferably completely embedded in the structural element in order to ensure good mechanical screening. Moreover, the sensor can be arranged in the vicinity of the neutral phase in order to keep the degree of the deformation as low as possible, should this be desired. In principle, the sensor may be arranged on the surface of the structural element or only partly be embedded into the structural element if the type of use of the orthopedic device and the structure of the sensor allow this.

A development of the invention provides for the sensor to be embodied as a strain gauge or as a piezo-element, wherein the piezo-element can also be utilized to generate electrical energy.

The conductors are insulated within the structural element and are also preferably insulated from one another in the opening-out region such that there can be unambiguous contacting and signal transmission.

In the end region, the conductors can be embodied as sliding contacts or contact tracks, which extend along at least one outer side of the end region. Contact tracks or sliding contacts allow contacting over a long region. Making electrical contact to the contacts corresponding to the contact surface's is very simple; the length of the structural element can be implemented easily by shortening in the region of the contact tracks; the mechanical properties of the structural element are not or only slightly adversely affected by the arrangement of the conductors as contact tracks on the outer side.

As an alternative or in addition thereto, it is possible for the conductors to be routed out of the structural element at the end face and open out there. The end-facing ends of the conductors form an end-facing termination of the conductors and hence the contact surface for corresponding contacts in the structural element, and so the arrangement of the contact surfaces remains unchanged, even if the length of the structural element changes.

The conductors can have a tubular design, which is advantageous particularly if the conductors are routed out on a end face, because said conductors can then simultaneously be formed as plug-in contacts and can accommodate the plugs.

Provision is likewise made for the structural element to be segmented, at least in regions, and for the segments to be embodied insulated from one another. This affords the possibility of allowing the segments to be embodied as conductors and being able to bring about mutually separate sensor-signal transmission or energy transmission. The structural element forms the conductors itself. The structural element is advantageously embodied in an electrically insulated fashion around the circumference thereof, particularly if the segments are embodied as conductors. The contact surfaces may likewise be insulated in the original state, wherein the insulation can be removed in the region of the electric contacting after shortening.

Forming an angular cross section in the structural element allows firstly to ensure anti-twist securing of the structural element on the components and secondly to provide sufficiently flat surfaces on which the contact surfaces can be formed.

The structural element can be produced from a carbon-fiber composite, a glass-fiber composite and/or a plastic. These materials allow high rigidity whilst having a low weight and an optionally desired electric conductivity and spring effect. In addition to an embodiment of the conductors as electrical conductors, provision is made for the conductors to be embodied as optical fibers. Here the arrangement of the conductors is of secondary importance, the type of measurement is likewise not decisive for the conductor routing in or on the structural element; for the purposes of electrical isolation it may be expedient for the signal or parts of the signal to be optically decoupled.

The sensors or sensor devices detect the loads within the structural element or the changes in the structure on the basis of e.g. changes in the resistance or via electrical pulses that change dependent on the load or are generated by a load. Strain gauges, optical strain gauges or sensors based on the piezo-effect can be arranged on or in the structural element. A variant of the sensor provides for a light source to be connected to a specially designed optical fiber, which is let into the structural part or embedded therein. The light source transmits light signals through the optical fiber or fibers, with, when a load is applied to the structural part, the light signals being modified by the optical fiber or fibers reflecting the signals differently. The type and scope of the deviation in the reflection then allows deductions to be made in respect of the type and scope of the load or on the deformation of the structural element. In the end regions of the structural element, the optical fiber can have a structure that induces no changes in the light signal in the case of a deformation; however, this is not necessarily mandatory. The optical fibers can also form the sensor themselves by fiber damage introduced in a targeted fashion or by burning absorption gratings.

The orthopedic device provides for an upper part and a lower part to be interconnected using an above-described structural element. Here, receptacle devices for fixing the structural element can be arranged on the upper part and/or the lower part, in which receptacle devices contacts are arranged, which are embodied in a corresponding fashion to the contact surfaces of the structural element in the assembled state. This affords the possibility of simply plugging the structural element into the receptacle devices and fixing it there, for example by screwing it in or by securely mounting it there using clamping devices.

The contacts and/or the contact surfaces can be embodied in a spring-loaded and displaceable fashion in the direction toward one another; in particular, the contacts are spring-loaded in the receptacle devices in order to be able to provide length-compensation and secure contacting even in the case of an unavoidable inaccuracy when shortening the structural element. This makes it possible to be able to fix the structural element with a certain amount of play within the receptacle devices. However, in principle it is also possible for the contact surfaces to be displaceable in the direction toward the contacts and to be embodied in a spring-loaded fashion, while the contacts are formed in a stationary fashion.

The contacts can be embodied as plug-in contacts, screw contacts or clamping devices; the contact can likewise be provided with a tip that pierces the insulation such that the complete insulation originally present is pierced by the assembly and a secure contact is only implemented at the point provided for this.

In the following text, exemplary embodiments of the invention will be explained in more detail on the basis of the figures, in which:

FIGS. 1a and 1b show views of a structural element with contact surfaces on the outer side;

FIGS. 2a and 2b show views of a structural element with conductors opening out at the end face;

FIGS. 3a to 3c show views of a structural element with integrated conductor segments;

FIGS. 4a to 4c show views of a structural element with a combination of an optical fiber and a segment conductor; and FIG. 5 shows an application of a structural element in an orthosis.

FIG. 1a shows, in a schematic lateral view, a structural element 1 made of a plastic, a fiber-composite material or the like. The structural element has an elongate, beam-like shape and has a substantially rectangular cross section; this can be seen from FIG. 1b. In the illustrated embodiment, the structural element 1 simultaneously forms a spring element.

A sensor 2 is integrated into the structural element 1; for example it has been molded, injected or laminated therein. By way of example, the sensor element 2 is embodied as a piezo-element, pressure sensor or strain gauge. Other sensors can also be arranged within the structural element 1; it is likewise possible for a plurality of sensors to be installed in one structural element 1.

Conductors 13 branch off the sensor element 2 and serve to transmit the signals generated within the sensor 2. In the embodiment illustrated in FIG. 1, the conductors 13 are embodied as electric conductors and contact a printed circuit board 4, which is arranged on a lateral surface of the structural element 1. The conductors 13 are connected to the contact surfaces 3, which are formed on the printed circuit board 4 and arranged on the outward-facing surface of the printed circuit board 4. The contact surfaces 3 and the printed circuit board 4 extend along an end region A of the structural element 1, which end region can be shortened according to individual needs. The overall length of the structural element 1 can be set via the length of the end region A such that it is possible to set the length of the resilient connection between an upper part and a lower part, or between two orthopedic components. This affords the possibility of allowing simple fitting to the individual needs of a patient or a user of an orthopedic device whilst leaving the upper and lower parts unchanged. The rigidity of the entire orthopedic device can likewise be changed by changing the length of the structural element 1.

In the exemplary embodiment as per FIG. 1a, the contact surfaces 3 form printed conductors on the outer side, which printed conductors are embodied as a type of sliding contact. The individual contact surfaces 3 are electrically insulated with respect to one another and distanced from one another in space such that the signals conducted via the contact surfaces 3 can be tapped by contacts 10 applied from the outside, which are illustrated in FIG. 1b. The contacts 10 are arranged in a receptacle 20 (only illustrated in part), into which the structural element 1 is inserted and into which it is fixed. In the original state, the entire structural element 1 can be provided with electrical insulation on the outside, which is only removed in the upper part and/or in the lower part in the region of the contacting by the contacts 10 after shortening to the desired length. This insulation can either be removed separately in a separate operation or by the contacts 10 themselves, which either remove or pierce the insulation during the assembly. To this end, it is advantageous if the contacts 10 are embodied to have a sharp edge or are embodied in a pointed fashion; the contacts 10 can likewise be embodied as screw contacts, which are mounted in a displaceable fashion in the direction toward the contact surfaces 3. Arranging the contact surfaces on the outside on the end region of the structural element 10 allows an individual adjustment of the length of the structural element to be achieved without having to shorten cables with plugs or plug receptacles attached thereto.

Furthermore, there is no need for a separate plug-in connection and it is no longer necessary to house and fix free cable ends or free lengths of cable. In the case of orthoses and prostheses in particular, free lying cables are a nuisance during use and constitute a potential hazard because open plug-in connections and cable connections as per the prior art can be separated or broken in everyday use.

The plan view as per FIG. 1b makes it possible to identify that the tapping contacts 10 are applied to the contact surfaces 3 from the outside. If the structural element 1 with its end region A, which was shortened to the desired length thereof, is inserted into a receptacle device, this is usually brought about by being pushed in such that the contacts 10 glide along the contact surfaces 3 and provide a good electrical contact. The contacts 10 can be mounted in a spring-loaded and elastic fashion in the direction toward the contact surfaces 3, and so production-related tolerances can easily be compensated for and moreover secure pressing of the contacts 10 onto the contact surfaces 3 is ensured.

A variant of the invention is illustrated in FIG. 2. FIG. 2a shows a schematic lateral view of the structural element 1 with the integrated sensor. Conductors 13 extend through the structural element 1 from the sensor 2 in the direction of a end-facing end and there they open up in the form of contact surfaces 3 within the cross section of the structural element 1; this can be identified in FIG. 2b. The conductors 13 are embodied as hollow profiles or tubes, which extend over the entire end region A. Contacts 10 that correspond to the contact surfaces 3 are embodied on a plug, which contacts are arranged and fixed on a receptacle device for the structural element 1. These contacts 10 can be inserted into the conductor tubes 13, and so there can be simple electrical contacting and secure locking. In addition to inserting pin-like contacts 10 into the conductors 13, it is possible for the conductors 13 to be embodied with a solid profile and for an electrical contact resting thereon to transmit the sensor signals or electrical signals from the sensor to the contacts 10. The contacts 10 can be embodied in a displaceable and spring-loaded fashion in the direction to the contact surfaces 3. The conductors and the contact surfaces 3 are electrically insulated from one another. Shortening the end region A affords the possibility of individually varying the overall length of the structural element 1, which is also embodied as a beam spring in this case, without there being a change in the assignment or in the transmission line. The conductors 13 and the contact surfaces 3 are also insulated with respect to the material of the structural element 1, because the material thereof can also be electrically conductive.

A further variant of the invention provides for the structural element 1 to be segmented. Here, the conductors 13 are embodied as parts of the structural element 1 and assume force-transmitting objects. Such a variant is illustrated in FIGS. 3a to 3c: FIG. 3a shows a schematic plan view, FIG. 3b shows a view of the end face and FIG. 3c shows a lateral view of the structural element 1. The sensor 2 is embedded in the structural element 1, as described in FIGS. 1 and 2. The structural element 1 consists of four conductor layers 13, which are separated from one another by electrical insulations 5. The electrically conductive segments 13, which for example consist of a carbon-fiber composite, form a structural unit together with the insulating layers 5, which structural unit assumes the mechanical functions of the structural element 1. Additionally, the conductively designed layers or segments 13 form the contact surfaces 3 on the outer edges or outer sides, from which contact surfaces the electrical signal can be tapped and transmitted via contacts 10, which for example are sliding contacts, screwed contacts or other contact devices provided with tips. In the illustrated exemplary embodiment, a total of four sliding contacts 10 are respectively arranged on the narrow sides of the structural element; it is also possible to tap the electrical signal on the end face or the two wide sides of the structural element 1. In this embodiment there can also be simple shortening in the end region A. The whole structural element 1 is expediently provided with electrical insulation in an embodiment of segments as conductors 13, which insulation is only pierced or removed in part at the contacts 10 when the structural element is inserted into the corresponding receptacle device or fixed thereto.

FIG. 4 provides a further variant with an integrated sensor 2, an optical fiber 13 and electrically conductive segments 13, which are separated from one another by an insulation layer 5. FIG. 4a shows a schematic plan view of the variant, FIG. 4b shows a plan view of the end face and FIG. 4c shows a schematic sectional view of the structural element 1 with an integrated sensor 2. It is possible to identify in FIGS. 4b and 4c that there is an insulation layer 5 between two conductive layers 13. By way of example, the conductive layers 13 are produced from a carbon composite or another conductive material. An optical fiber, connected to the sensor 2, is embedded between the two conductive layers 13. The conductive elements 13 are connected to the sensor 2 via contact pins 6. As an alternative to a fully conductive embodiment of the conductive elements 13, it is also possible that only the surface of the structural element is embodied in an electrically conductive fashion in the region of the end region A and forms the contact surfaces there.

The optical fiber 13 ends on the end face at a contact surface 3, in respect of which an optical-fiber sensor is arranged in a corresponding fashion on a receptacle device 20. The light signals transmitted via the optical fiber 13 and the contact surface 3 are recorded and transmitted by the optical-fiber sensor 11, or optionally converted into electrical signals by the latter.

Contact surfaces 10 are provided on the receptacle device 20, into which the structural element 1 is inserted, which contact surfaces come into contact with the contact surfaces 3 on the outer side of the end region A. The contact surfaces 10 on the receptacle device 20 bring about large-area rest on the mutually opposing outer sides of the structural element 1. Here the contact surfaces 3 can also at first be embodied in an insulated fashion and only be de-insulated for the purpose of the assembly.

FIG. 5 illustrates an orthopedic device 100 in the form of a leg orthosis. The leg orthosis 100 has a receptacle device 101 for an upper leg and a receptacle device 102 for a lower leg. The two receptacle devices 101, 102 are interconnected in a pivotable fashion via joint devices 103 in the region of the natural axis of the knee. A receptacle 20 is arranged on the receptacle device 102 for the lower leg and it is plugged into a structural element 1 in the form of a lower leg splint. A foot rest 104 onto which the patient's foot can be placed is shaped onto the distal end of the structural element 1. The receptacle devices 101, 102 can be made from a plastic or a composite material. The receptacle can be formed integrally on the receptacle device 102 for the lower leg, or it can be subsequently fixed thereto. The structural element 1 is embodied in the form of a beam and has a sensor device (not illustrated in any more detail), which is connected to conductors integrated with the structural element 1. The sensor signals are then recorded via contacts (likewise not illustrated) within the receptacle 20 and transmitted to an evaluation unit.

In order to render an individual production of the orthosis 100 unnecessary, the receptacle devices 101, 102 can have a substantially prefabricated design. The upper leg receptacle device 101 either can be shortened at the proximal end or has such a short design that it is also possible to equip patients with very short upper legs therewith. Even then the upper leg receptacle 101 is generally long enough to ensure secure fixation even in the case of large patients.

In order also to allow a length modification between the foot rest 104 and the joint device 103, so that the orthosis 100 can be fitted correctly to the patient, the structural element 1 has a design that allows shortening such that the distance between the foot rest 104 and the joint axis 103, which is important to the function of the orthosis, can be modified individually without requiring complicated reworking of the electrical contacting. In the present embodiment, the structural element 1 is arranged toward the back and it can have resilient properties, but in principle it is also possible for the sensors not be arranged in the beam-like part of the structural element 1 but in the region of the foot rest 104. It is also possible for the foot rest 104 to be formed separately and be able to be fixed to the structural element 1.

In addition to orthoses, the structural elements 1 can also be used in prostheses; the application purpose is not restricted to orthoses or prostheses for lower extremities, rather the structural elements 1 can be used wherever a length modification option for an orthopedic device is necessary and sensor data should be registered and transmitted from the orthopedic device.

The invention claimed is:

1. A structural element for an orthopedic device, comprising:
   a plurality of conductors integrated into the structural element and extending along an end region of the structural element, terminating at the end region, and forming electrical contact surfaces at the end region that permit a modification in effective length of the structural element;
   at least one sensor arranged in or on the structural element, the sensor being connected to the conductors for transmitting at least one of energy and sensor signals;
   wherein the structural element is configured to mechanically connect to components of the orthopedic device.

2. The structural element as claimed in claim 1, wherein the sensor is completely embedded into the structural element.

3. The structural element as claimed in claim 1, wherein the sensor is embodied as a strain gauge, optical strain gauge or piezo-element.

4. The structural element as claimed in claim 1, wherein the structural element is embodied as a spring element.

5. The structural element as claimed in claim 1, wherein the conductors within the structural element and the contact surfaces in the end region are insulated from one another.

6. The structural element as claimed in claim 1, wherein the contact surfaces in the end region are embodied as sliding contacts or contact tracks, which extend along at least one outer side of the end region.

7. The structural element as claimed in claim 1, wherein the conductors are routed out of the structural element and terminate at an end face of the structural element.

8. The structural element as claimed in claim 1, wherein the conductors have a tubular design.

9. The structural element as claimed in claim 1, wherein the structural element is segmented, at least in regions, and the segments are insulated from one another and embodied as conductors.

10. The structural element as claimed in claim 1, wherein the structural element is electrically insulated around a circumference of the structural element.

11. The structural element as claimed in claim 1, wherein the structural element, at least in part, has an angular cross section.

12. The structural element as claimed in claim 1, wherein the structural element is produced from at least one of a carbon-fiber composite, a glass-fiber composite and a plastic.

13. The structural element as claimed in claim 1, wherein the structural element is embodied such that it can be shortened.

14. The structural element as claimed in claim 1, wherein the sensor is embodied as a light source with at least one optical fiber coupled thereto, wherein the optical fiber modifies a light signal from the light source dependent on a load on the structural element.

15. An orthopedic device with an upper part and a lower part, which are interconnected via the structural element as claimed in claim 1.

16. The orthopedic device as claimed in claim 15, wherein receptacle devices for fixing the structural element are arranged in at least one of the upper part and lower part, in which receptacle device contacts are arranged, which are embodied in a corresponding fashion to the contact surfaces of the structural element in an assembled state.

17. The orthopedic device as claimed in claim 15, wherein at least one of the contacts and the contact surfaces are embodied in a spring-loaded and displaceable fashion in a direction toward one another.

18. The orthopedic device as claimed in claim 15, wherein the contacts are embodied as plug-in contacts, screw contacts, clamping apparatuses or with a tip that pierces insulation of the conductors.

19. An orthopedic device having a structural element, the structural element comprising:
   a structural member configured for mechanical connection to components of the orthopedic device;
   a plurality of conductors integrated into the structural member and which extend along an end region of the support member, terminate at the end region, and form contact surfaces that permit modification of an effective length of the structural element;
   at least one sensor mounted to the structural member and connected to the conductors, the at least one sensor being configured to transmit at least one of energy and sensor signals.

20. An orthopedic device having a structural element, the structural element comprising:
   a structural member configured for mechanical connection to components of the orthopedic device;
   at least one optical fiber integrated into the structural member and extending along an end region of the support member, the at least one optical fiber terminating at an end face of the support member;
   at least one sensor mounted to the structural member and arranged to receive signals from the at least one optical fiber, the at least one sensor being configured to transmit at least one of energy and sensor signals.

21. An orthopedic device having a structural element, the structural element comprising:
   a structural member configured for mechanical connection to components of the orthopedic device;
   a plurality of conductors integrated into the structural member and which extend along an end region of the support member, terminate at the end region, and form sliding contact surfaces that permit length adjustability of the structural element without shortening the structural member;

at least one sensor mounted to the structural member and connected to the conductors, the at least one sensor being configured to transmit at least one of energy and sensor signals.

* * * * *